United States Patent
Meltsner et al.

(10) Patent No.: US 10,850,119 B2
(45) Date of Patent: Dec. 1, 2020

(54) INTERACTIVE COMPUTER-AIDED EDITOR FOR COMPENSATORS USED IN RADIOTHERAPY TREATMENT PLANNING

(75) Inventors: Michael A. Meltsner, Fitchburg, WI (US); Ying Xiong, Naperville, IL (US); Michael Kaus, Madison, WI (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 720 days.

(21) Appl. No.: 13/388,061

(22) PCT Filed: Jul. 9, 2010

(86) PCT No.: PCT/IB2010/053156
§ 371 (c)(1),
(2), (4) Date: Jan. 31, 2012

(87) PCT Pub. No.: WO2011/024085
PCT Pub. Date: Mar. 3, 2011

(65) Prior Publication Data
US 2012/0157746 A1     Jun. 21, 2012

Related U.S. Application Data

(60) Provisional application No. 61/238,322, filed on Aug. 31, 2009.

(51) Int. Cl.
*A61N 5/10* (2006.01)
*G16H 20/40* (2018.01)

(52) U.S. Cl.
CPC .............. *A61N 5/103* (2013.01); *G16H 20/40* (2018.01); *A61N 2005/1074* (2013.01); *A61N 2005/1096* (2013.01)

(58) Field of Classification Search
CPC .... A61N 2005/1074; A61N 2005/1096; A61N 5/103
(Continued)

(56) References Cited

U.S. PATENT DOCUMENTS

| 7,333,591 B2 | 2/2008 | Earl et al. |
| 8,466,916 B2 | 6/2013 | Engel et al. |
| 2005/0111621 A1 | 5/2005 | Riker et al. |

FOREIGN PATENT DOCUMENTS

| JP | 10192427 A | 7/1998 |
| JP | 2005237694 A | 9/2005 |

(Continued)

OTHER PUBLICATIONS

Liu et al., 'Image-assisted knowledge discovery and decision support in radiation planning,' 2007, Comp. Med. Imag. , vol. 31, p. 311-321.*

(Continued)

*Primary Examiner* — Eliza W Osenbaugh-Stewart (57) ABSTRACT

When constructing compensators for radiation therapy using ion or proton radiation beams, a computer-aided compensator editing method includes overlaying an initial 3D compensator model on an anatomical image of a target mass (e.g., a tumor) in a patient, along with radiation dose distribution information. A user manipulates pixels or voxels in the compensator model on a display, and a processor automatically adjusts the dose distribution according to the user edits. The user iteratively adjusts the compensator model until the dose distribution is optimized, at which time the optimized compensator model is stored to memory and/or output to a machining device that constructs a compensator from the optimized model.

20 Claims, 11 Drawing Sheets

(58) Field of Classification Search
USPC .......................................... 250/492.3, 515.1
See application file for complete search history.

(56) References Cited

FOREIGN PATENT DOCUMENTS

| WO | 03092789 | A2 | 11/2003 |
|---|---|---|---|
| WO | 2005062790 | A2 | 7/2005 |
| WO | 2008114159 | A1 | 9/2008 |
| WO | 2008134869 | A1 | 11/2008 |

OTHER PUBLICATIONS

Lim et al., 'An optimization framework for conformal radiation treatment planning,' Dec. 2002, Inform. Jour. Comp., vol. 49, p. 1-36.*

Bortfeld et al., 'Effects of Motion on the Total Dose Distribution' Jan. 2004, Seminars in Radiation Oncology, vol. 14, No. 1, pp. 41-51.*

Javedan et al., 'Compensator-based intensity-modulated radiation therapy for malignant pleural mesothelioma post extrapleural pneumonectomy' Fall 2008, Journal of Applied Clinical Medical Physics, vol. 9, No. 4, p. 98-109.*

Bussiere, M. R., et al.; Treatment Planning for Conformal Proton Radiation Therapy; 2003; Technology in Cancer Research & Treatment; 2(5)389-399.

Goodband, J. H., et al.; A mixture of experts committee machine to design compensators for intensity modulated radiation therapy; 2006; Pattern Recognition; 39(9)1704-1714.

Jurkovic, S., et al.; An alternative approach to compensators design for photon beams used in radiotherapy; 2007; Nuclear Instruments and Methods in Physics Research; A 580:530-533.

Kanematsu, N., et al.; Tumour shapes and fully automated range compensation for heavy charged particle radiotherapy; 2004; Phys. Med. Biol.; 49:N1-N5.

Li, Y., et al.; A novel patch-field design using an optimized grid filter for passively scattered proton beams; 2007; Phys. Med. Biol.; 52:N265-N275.

Petti, P. L.; New compensator design options for charged-particle radiotherapy; 1997; Phys. Med. Biol.; 42:1289-1300.

Urie, M., et al.; Compensating for heterogeneities in proton radiation therapy; 1983; Phys. Med. Biol.; 29(5)553-566.

Wagner, M. S.; Automated range compensation for proton therapy; 1982; Med. Phys.; 9(5)749-752.

Wilks, R. J., et al.; The use of a compensator library to reduce dose inhomogeneity in tangential radiotherapy of the breast; 2002; Radiotherapy and Oncology; 62:147-157.

Li, J., et al.; Research of Three-Dimension Radiation Treatment Planning System; 2009; Journal of Chinese Computer Systems; 30(7)1404-1411.

* cited by examiner

INTERACTIVE COMPUTER-AIDED EDITOR FOR COMPENSATORS USED IN RADIOTHERAPY TREATMENT PLANNING

CROSS REFERENCE TO RELATED APPLICATIONS

This application claims the benefit of U.S. provisional application Ser. No. 61/238,322 filed Aug. 31, 2009, which is incorporated herein by reference.

The present application finds particular utility in radiotherapy treatment planning (RTP) systems. However, it will be appreciated that the described technique(s) may also find application in other types of therapy planning systems, other computer-aided editing systems, and/or other therapeutic applications.

In proton and heavy-ion therapy, the particles have the property of "stopping" in the medium after a certain depth based on the energy and properties of the medium, particle, and delivery machine. The maximum dose delivered to the medium is delivered at the so called "Bragg Peak" at the end of the particles' range.

In proton and ion beam radiotherapy, a compensator is typically disposed between the radiation source and the subject. The compensator is custom manufactured for each patient. It typically takes the form of a plexiglass layer with different thicknesses in different regions in order to compensate for the different tissues between the beam and the target at different beam angles such that a uniform dose is delivered to the target, i.e. to position the Bragg Peak on the target.

In external beam radiotherapy treatment planning, the compensator is custom-designed for each patient to adjust the radiation dose delivered to that patient. The initial design is typically calculated and optimized within the treatment planning system and displayed via a matrix-style representation of the thickness values of the compensator. This matrix provides little useful feedback to the user in regard to the compensator's design. Generally, the user is allowed to change the values of any one of the individual pixels in a spreadsheet-entry manner. However, these changes are difficult to justify and quantify. The user may want to edit the compensator for reasons such as: to eliminated hot or cold spots of radiation dose within the patient; to soften the gradient between neighboring pixels which, if too steep, could cause vast changes in dose delivered to the target or organs at risk in the event of slight patient setup errors; to widen or narrow the compensator shape to cover more or less of the target organ; or because the dose distribution provided by the initial computer algorithm is not acceptable.

Proton and ion therapy have many clinical advantages compared to gamma radiation photons, for example. Proton and ion beams can be combined in novel ways to deliver a uniform dose distribution to a complex target in medium. One of these techniques is the so called "Patch Field" technique in which two or more beams are essentially perpendicular to each other. For example, the "through" beam irradiates longitudinally and the "patch" beam irradiates laterally. The mechanical properties of the patch and the through beams are adjusted to provide a uniform dose in the overlap region, i.e. to the target. The patch system is a known technique used in radiotherapy. However, the tools to implement and optimize this technique are not advanced.

In ion or proton based therapy (henceforth collectively referred to as "ion therapy") specifically, the initial design is typically calculated and optimized within the treatment planning system with a single objective—to conform the dose to the distal edge of the target tissue. This limits the user's ability to shape the dose distribution from the ion therapy source to the patient. Although manual edits may be made to the compensator pixels, such edits are based on trial and error and would be considered a forward planning approach to the compensator design. The initial compensator design in ion therapy may not be ideal when multiple factors are considered. For example, if the target tissue is in close proximity to an organ-at-risk (OAR), then the uniform coverage of the target may force too much dose to spill into the OAR. Further, any margins that are added to the target's shape may cause further increases to the dose within the OAR. Ideally, the user may want to examine certain trade-offs to the dose distribution to the target with respect to the dose to the surrounding tissues.

Complex target coverage is another major concern in radiotherapy treatment planning. The radiation dose delivered to the target anatomy needs to be adequate while minimizing the dose to neighboring organs at risk. When the shape of the target is complex, multiple beams may be used to cover separate portions of the target. In this case, overlapping dose from the beams may create an unwanted hotspot and reduced uniformity within the target tissue.

There is an unmet need in the art for systems and methods that facilitate interactively displaying the compensator in 3 dimensions, including the patient anatomy and dose distribution, to aid the user in manually adjusting the compensator pixels, and the like, thereby overcoming the deficiencies noted above.

In accordance with one aspect, a system that facilitates optimizing a computer-generated 3D compensator model for use in radiotherapy treatment planning includes a graphical user interface (GUI) including a display and a user input device, and a processor that executes computer-executable instructions stored in a memory. The instructions include displaying on the display, to a user, a compensator model, receiving user input from the user input device comprising edits to the compensator model, optimizing the compensator model based on the user input, and storing the optimized compensator model to the memory or computer-readable storage medium.

In accordance with another aspect, a method of computer-aided compensator model optimization for compensators used in radiotherapy treatment includes displaying a compensator model on a patient image of an anatomical region of a patient, receiving user input edits to the compensator model, and updating the compensator model based on the user input. The instructions further include storing the updated compensator model to memory or computer-readable storage medium.

In accordance with another aspect, a method of optimizing radiation dose distribution for an irregularly-shaped target mass in a patient while mitigating radiation dose to a nearby organ includes identifying lateral and distal sections of a computerized model of the target mass and a junction between the lateral and distal sections, and making a virtual cut in the model along the junction. The method further includes iteratively adjusting contours of the lateral and distal sections in order to optimize a radiation dose distribution, and displaying dose distribution overlaid on a patient image that includes the target mass for user evaluation during dose distribution optimization.

One advantage is that compensator manufacture is improved.

Another advantage resides in minimizing unnecessary radiation dose to the patient.

Another advantage resides in simplifying compensator design, which improves design precision.

Still further advantages of the subject innovation will be appreciated by those of ordinary skill in the art upon reading and understand the following detailed description.

The drawings are only for purposes of illustrating various aspects and are not to be construed as limiting.

The systems and methods described herein, in one embodiment, relate to a computerized system that displays dose distribution of a radiotherapy beam overlaid onto a projection of the compensator pixels and patient anatomy for detailed visualization. Additionally, editing tools are provided to adjust and edit the compensator based on the user intent while interactively displaying the changes to the dose distribution.

In another embodiment, a computerized algorithm accounts for the target shape, beam dose, and properties of the delivered particles to provide a uniform dose distribution. A graphical user interface and editing tools facilitate manipulation of the beam parameters to ensure acceptable target irradiation.

In another embodiment, computerized editing tools and algorithms are provided for compensator design and optimization. The algorithms factor in user-specified goals and/or objectives for the desired dose to the patient, target and surrounding tissues in proton and ion based therapy.

Figure 1:
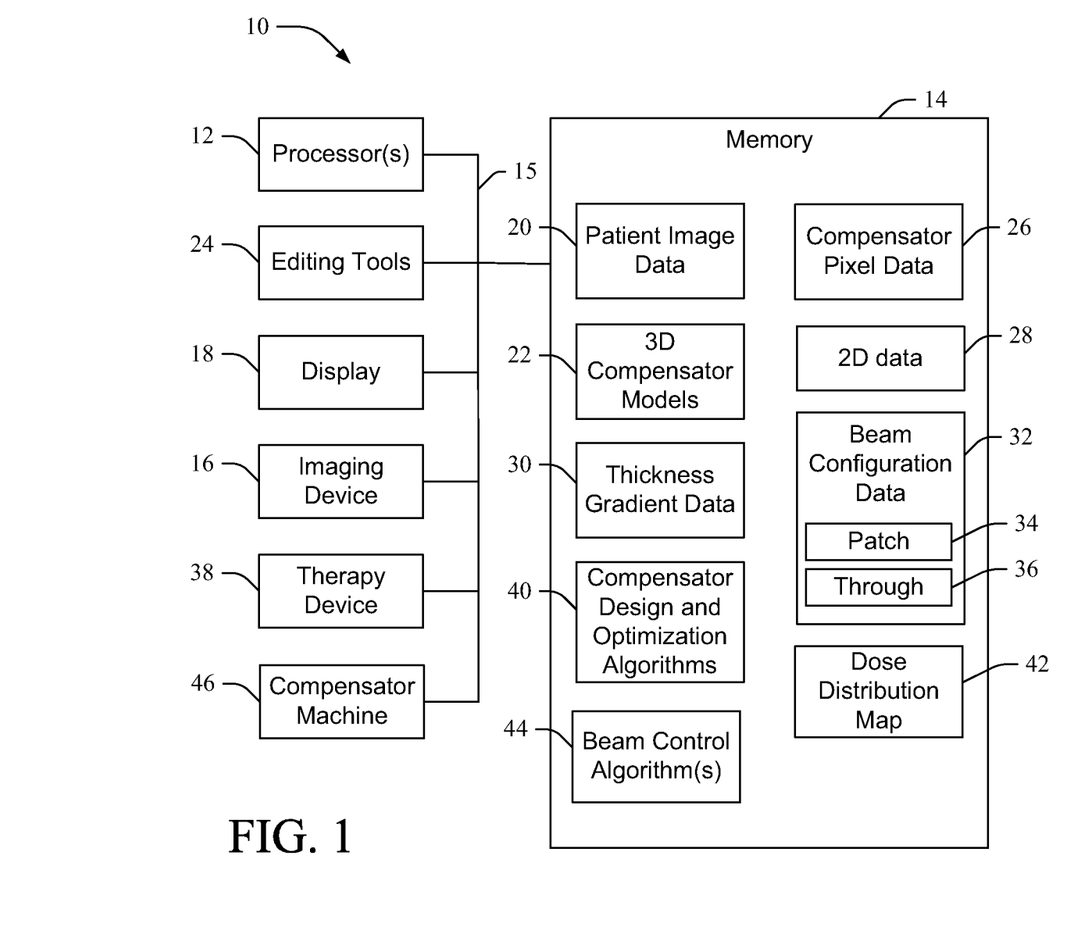
FIG. 1 illustrates a system for editing a compensator used during radiotherapy planning and radiation dose application to a patient.

FIG. 1 illustrates a system 10 for editing a compensator used during radiotherapy planning and radiation dose application to a patient. The system includes a processor 12 that executes, and a memory 14 or other computer-readable media that stores, computer-executable instructions for carrying out the various methods and/or techniques described herein. The processor and memory are coupled to each other via a bus 15, which is also coupled to an imaging device 16 (e.g., a computed tomography device, a magnetic resonance imaging device, a nuclear scanning device, etc.) and a display 18. The imaging device generates scan data of a subject or patient, which is reconstructed by a reconstruction processor to generate patient image data 20 that is stored in the memory 14 and displayed on the display 18. In one embodiment, the processor(s) 12 include a reconstruction processor that executes reconstruction algorithms or the like.

The memory 14 also stores one or more 3D compensator models 22. A user selects a compensator model 22 using an editing tool 24, which may include a mouse, stylus, keyboard, or other input device. The memory additionally stores compensator pixel data 26, 2D cross-sectional plane data 28 corresponding to slices of the compensator model 22, and compensator gradient thickness data 30. Additionally, beam configuration data 32 is stored in the memory, and includes patch parameters 34 and/or algorithms and through parameters 36 and/or algorithms for the radiation beam to be applied to a target mass in the patient. The beam configuration data is provided to a therapy device 40 that generates the radiation beam when irradiating the target tissue in the patient.

The memory further stores one or more algorithms (e.g., computer-executable instructions) for compensator design and optimization. For instance, the 3D compensator models can be pre-generated or can be generated specifically for each patient therapy treatment. Using the editing tools, the user adjusts a selected model on the display, and the revisions are stored 22 as different versions of the compensator model. Each edit input by the user causes the processor to execute the optimization algorithm(s) and adjust the model accordingly. The user then reviews the edited model(s) and accepts or rejects the changes. If the user accepts the changes, the revised model is stored to the memory for use during the radiation treatment event.

According to one embodiment, a user-selected compensator 22 is projected onto the patient anatomy image displayed on the display 18, along with a dose distribution map 42 in a beam's eye view display. Using the editing tools 24, the user steps through anatomical slices of the patient anatomy image 20, and the projection of the compensator 22 is adjusted accordingly by the processor 12. In this manner, an individual compensator pixel can be traced back to the dose distribution and anatomical features.

The editing tools 24 permit the user to edit the compensator pixels 26 in the beam's eye view representation. The user may change the compensator pixels by adding, subtracting, averaging, etc. a value. Furthermore, the user-entered changes will be updated in the 3-dimensational model of the compensator. In addition to the beam's eye view and 3-dimensional model, the 2-dimensional cross-sectional planes 28 of the compensator aid the user in visualization of the thickness gradients 30 of the compensator 22. After the user edits the compensator, the processor 12 recomputes the dose distribution 42 of the beam with the revised compensator, and the user compares the results to the original. The user may then "undo" changes or continue with further editing. When completed, the edits can then be saved and copied to the original beam meant for delivery.

According to another embodiment, one or more beam control algorithm(s) 44 are executed by the processor 12 to automatically adjust the beam configuration 32 and corresponding therapy device 38 (e.g., an ion beam generator, a proton beam generator, or the like) parameters to account for the target shape, beam dose, and properties of the delivered particles to provide a uniform dose distribution to the target. The "patch" junction in the target tissue is determined, and a 3 dimensional "cut" of the target is made by the beam control algorithm 44. The contours for the patch and the through beam's targets are treated separately and may be manually or automatically adjusted by the beam control algorithm based on the dose distribution and properties of either the patch or through beams. The user interacts with the region of interest (ROI) contours that outline the target, as well as with the beam parameters, to tailor the dose until the user is satisfied. The user can display the updated dose distribution map 42, which shows radiation dose delivered to the target with each compensator edit, for evaluation and re-optimization.

In another embodiment, the user is provided with the display 18 and editing tools 24 (e.g., a graphical user interface (GUI)) with which to set goals or objectives for the dose distribution to certain points, organs or regions of the patient. The user can specify dose intensity as a range, uniformity, or as a biological equivalent effect that a particular region should receive, as well as a rank for each one of these objectives, which conveys the relative importance of meeting that objective. The processor 12 then executes the compensator design and optimization algorithms 40 to design a compensator, and/or adjusts the beam configuration parameters including, but not limited to, the range and modulation, margins, and energy of the beam to attempt to meet the objectives. Further, the user may include certain uncertainties such as patient motion and density conversion. After the processor is finished calculating, the user is given the opportunity to review the results and adjust the parameters further, which may necessitate a re-optimization.

The GUI allows user interaction with the software code and algorithms used to optimize the therapy treatment. The algorithms can be coded to determine a solution to the user-defined objectives by computing the dose distribution and adjusting the compensator pixels and therapy device parameters. A review interface allows the user to view the results of the optimization.

In another embodiment, instead of entering in objectives in a "text-based" manner, the user can "draw" the desired dose distribution on the display screen (e.g., using an input device such as a mouse or stylus), and the algorithm matches the graphical representation of the dose by adjusting and optimizing the aforementioned parameters relating to the dose delivery, such as the compensator, modulation, etc.

The system 10 also includes a compensator machine 46 that receives finalized compensator models that have been approved by the user, and which constructs the actual compensators according to the design parameters of the models. In one embodiment, the compensator machine is located at the same site as the system 10 and the compensators are generated on site. In another embodiment, the compensator machine is located remotely from the system 10 (e.g., in a different room, building, city, state, country, etc.), and approved compensator model data is stored to a computer-readable storage medium (e.g., a disk, a memory stick, or some other suitable storage medium) at the system site and transported to the compensator machine site where the model data is uploaded into the compensator machine. Alternatively, 3D compensator model data can be electronically transferred to the compensator machine, such as by email, wireless communication link, infrared, radio frequency, or the like.

As mentioned above, the system includes the processor(s) 12 that executes, and the memory 14 that stores, computer executable instructions for carrying out the various functions and/or methods described herein. The memory 14 may be a computer-readable medium on which a control program is stored, such as a disk, hard drive, or the like. Common forms of computer-readable media include, for example, floppy disks, flexible disks, hard disks, magnetic tape, or any other magnetic storage medium, CD-ROM, DVD, or any other optical medium, RAM, ROM, PROM, EPROM, FLASH-EPROM, variants thereof, other memory chip or cartridge, or any other tangible medium from which the processor 12 can read and execute. In this context, the system 10 may be implemented on or as one or more general purpose computers, special purpose computer(s), a programmed microprocessor or microcontroller and peripheral integrated circuit elements, an ASIC or other integrated circuit, a digital signal processor, a hardwired electronic or logic circuit such as a discrete element circuit, a programmable logic device such as a PLD, PLA, FPGA, Graphical card CPU (GPU), or PAL, or the like.

Figure 2:
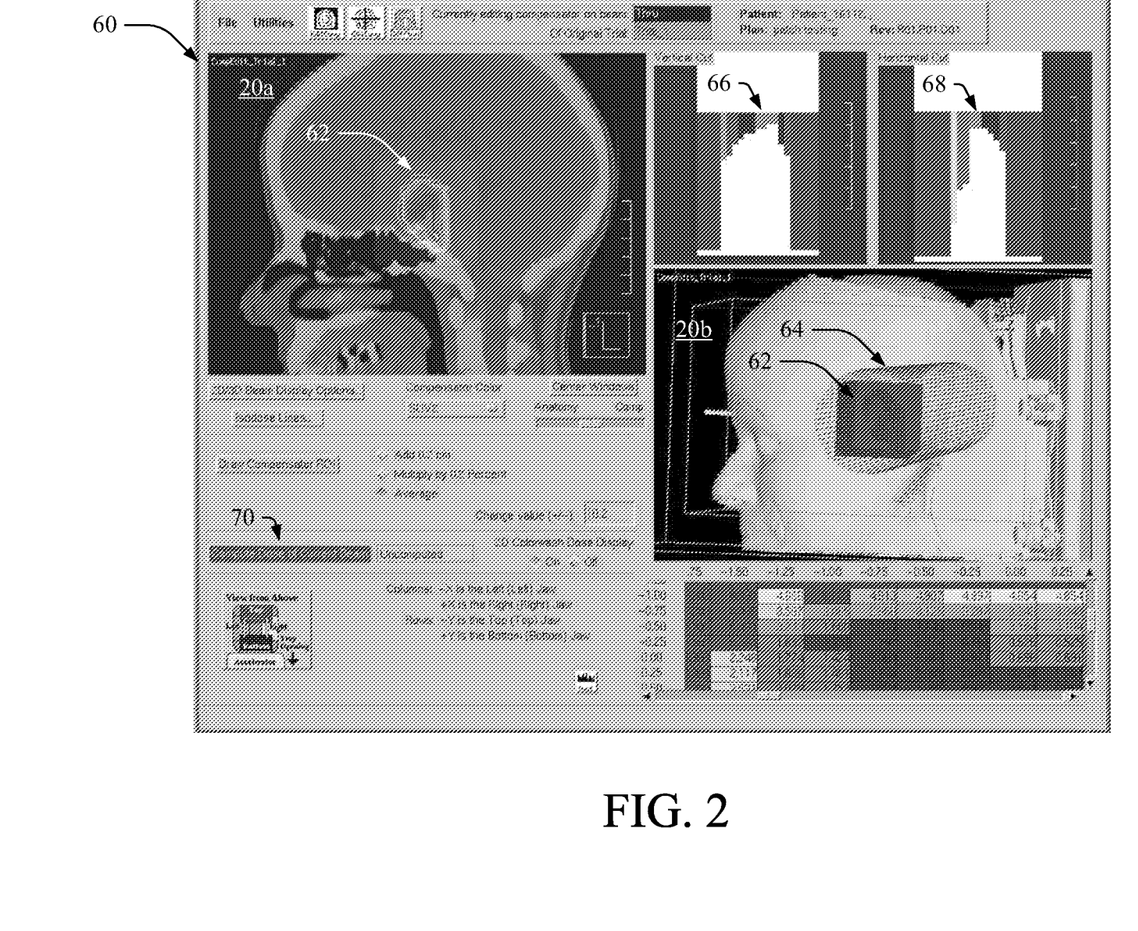
FIG. 2 is an example of a compensator editing graphical user interface (GUI) such as may be displayed on the display of FIG. 1.

FIG. 2 is an example of a compensator editing GUI 60 such as may be displayed on the display 18 of FIG. 1. The GUI includes a one or more patient images 20a, 20b. The patient image 20a shows a virtual compensator 62 overlaid on the patient image 20a. The patient image 20b shows a beam's eye view of a radiation beam 64 projected into the patient to irradiate a target mass through the compensator 62. Also shown are a 2D vertical slice 66 through the compensator, and a 2D horizontal slice 68 through the compensator. The GUI permits a user to adjust the virtual compensator so achieve a desired radiation dose to the target mass. Once the user is satisfied that the compensator has been refined to successfully apply an appropriate dose of radiation to the target mass, while mitigating radiation dose to organs at risk or other tissue for which radiation dose is undesirable, the virtual compensator model 62 configuration is saved to memory and used for constructing a physical compensator for use during radiotherapy treatment of the patient.

Figure 3:
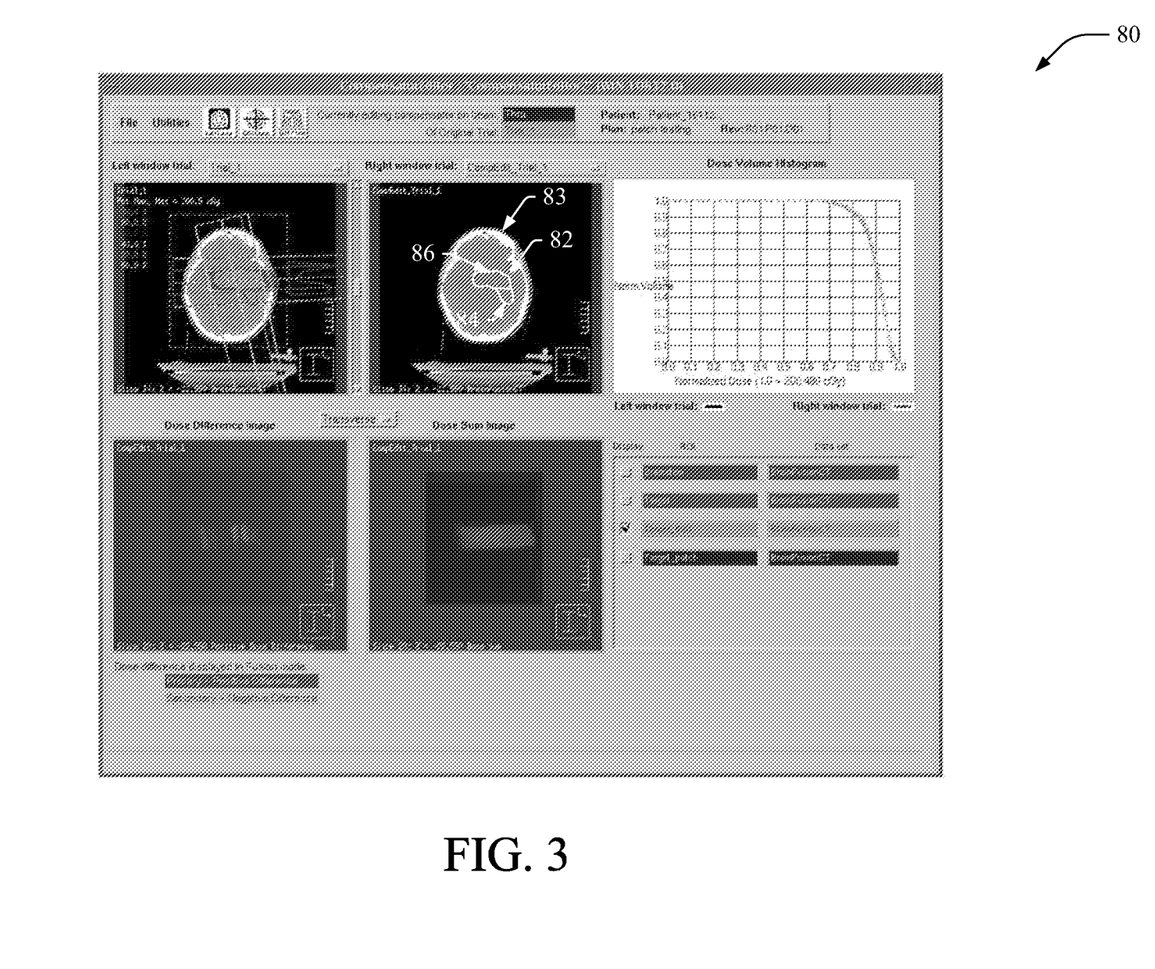
FIG. 3 is an example of a compensator editing GUI that includes a generally L-shaped target mass in a patient's cranium, wherein the mass is divided into a through (distal) region and a patch (lateral) region to be individually irradiated during a radiotherapy treatment.

FIG. 3 is an example of a compensator editing GUI 80 that includes a generally L-shaped target mass 82 in a patient's cranium 83, wherein the mass is divided into a through region 84 and a patch (lateral) region 86 to be individually irradiated during a radiotherapy treatment.

Figure 4:
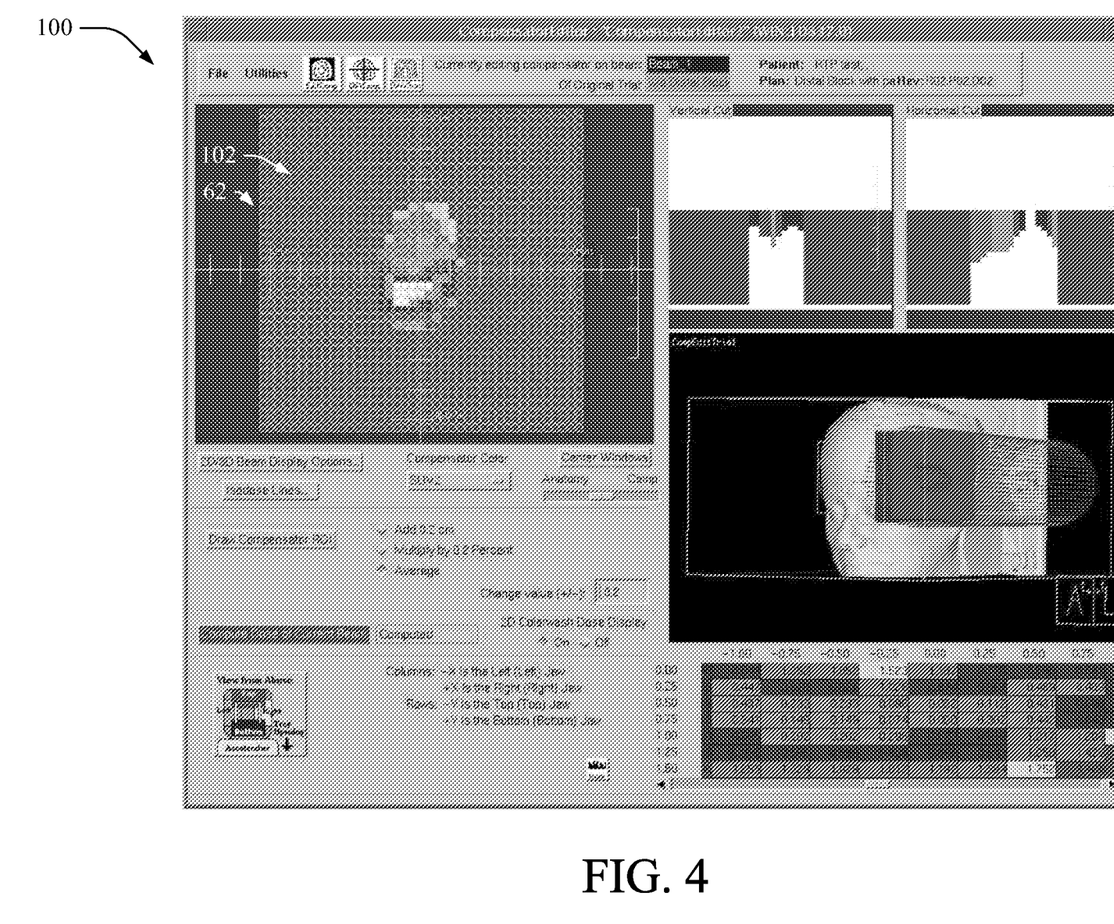
FIG. 4 is a screenshot of a GUI showing a top-down view of the virtual compensator model, which comprises a plurality of pixels.

FIG. 4 is a screenshot of a GUI 100 showing a top-down view of the virtual compensator model 62, which comprises a plurality of pixels 102. Each pixel corresponds to a point on a real compensator that is to be generated using the model (e.g., by the compensator machine 46 of FIG. 1). Once the model 62 is approved by a user, it is stored to memory and output to the compensator machine.

Figure 5:
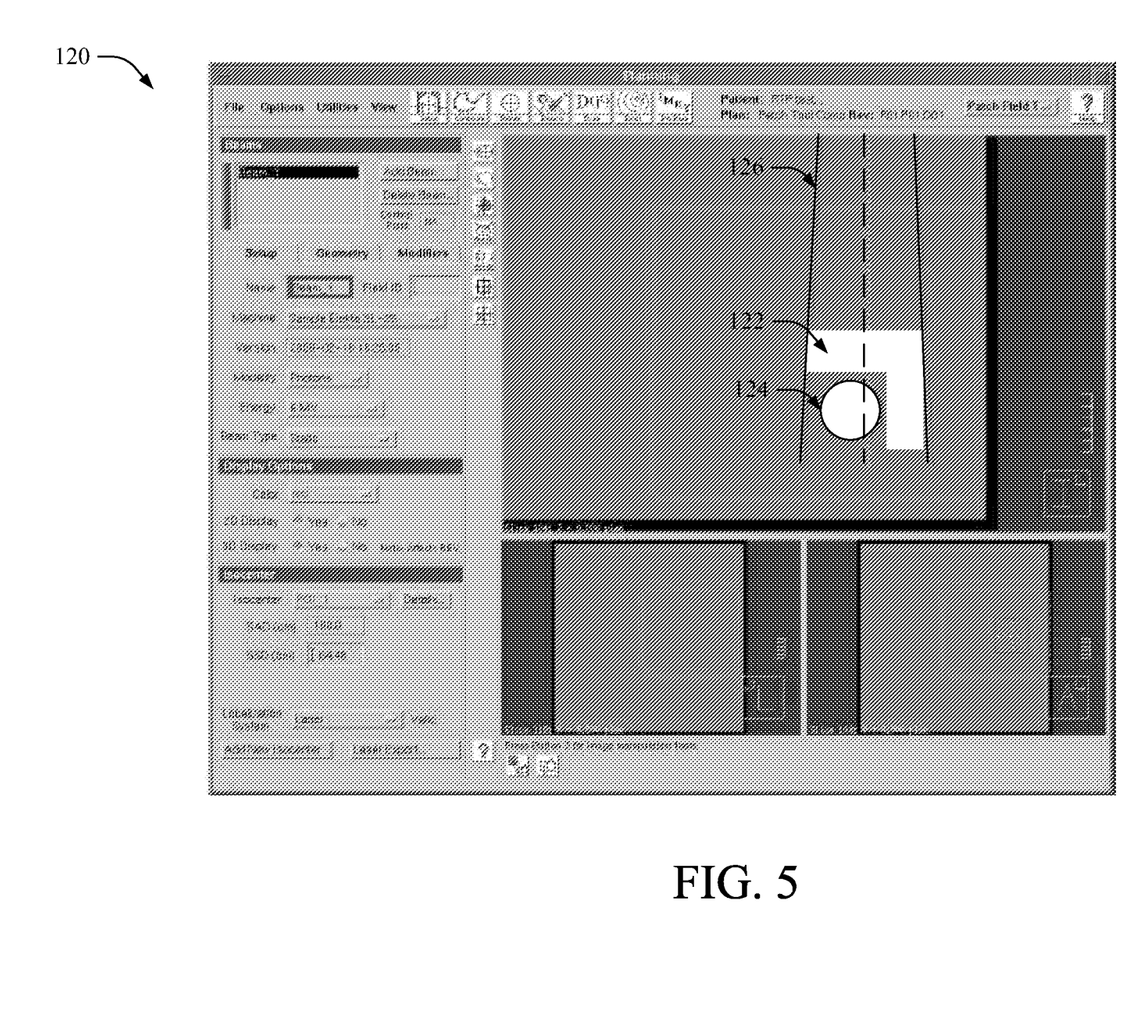
FIG. 5 is a screenshot of a GUI in which a substantially L-shaped target mass is positioned in close proximity to an organ at risk.

FIG. 5 is a screenshot of a GUI 120 in which a substantially L-shaped target mass 122 is positioned in close proximity to an organ at risk 124 (e.g., an organ that is not to be irradiated during irradiation of the target mass). An ion beam 126 is shown as covering the entire target mass, in which case the organ at risk will be unnecessarily irradiated. However, with an appropriately designed compensator, the Bragg Peak will be positioned in the arm of the target region and few ions will reach the organ at risk.

Figure 6:
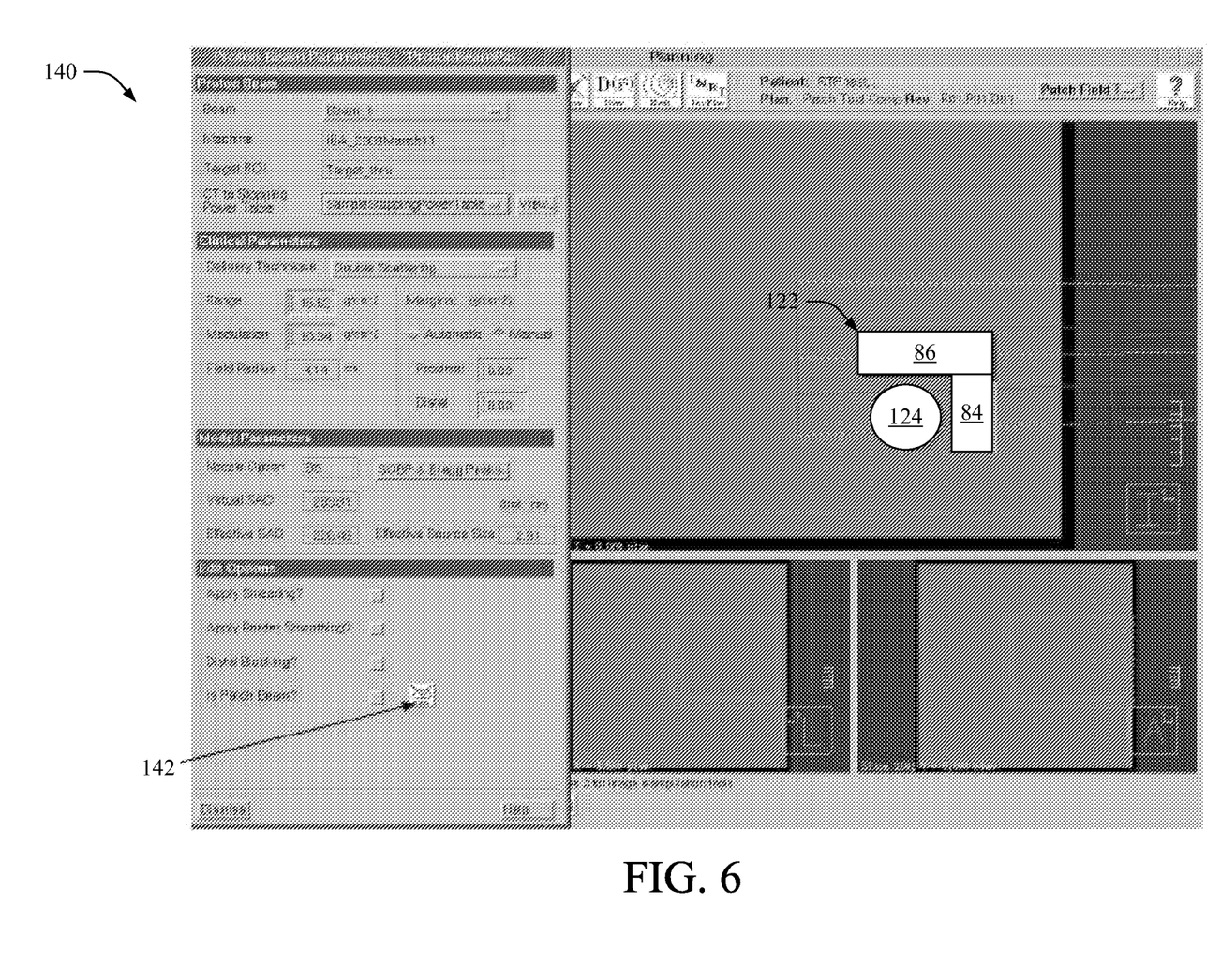
FIG. 6 is a screenshot of a GUI including a "patch" tool that a user selects to cause the processor of FIG. 1 to execute beam configuration algorithms and adjust beam configuration data to generate patch beam data and through beam data, which are used to irradiate a patch portion of the target mass and a through portion of the target mass, respectively.

FIG. 6 is a screenshot of a GUI 140 including a "patch" tool 142 that a user selects (e.g., clicks on, etc.) to cause the processor 12 of FIG. 1 to execute beam configuration algorithms and adjust beam configuration data 32 to generate patch beam data 34 and through beam data 36 (see FIG. 1), which together deliver a substantially uniform dose to both the patch region 84 and the through region 86. The patch and through technique more precisely irradiates the target mass 122 while sparing the organ at risk 124.

Using the patch and through technique, multiple beams are employed to cover a complicated target mass with good conformity and minimal dose to organs at risk. The algorithm includes delineating the target mass, which may be performed by a user by marking or outlining the mass on a patient image (e.g., using a stylus, a mouse, or some other input tool). The patch tool 142 is initiated and automatically splits the target mass into the patch and through portions. Alternatively, this step can be performed manually by the user. In one embodiment, 50% of the total irradiation beam is provided laterally through the through portion 86, and the remaining 50% is provided distally through the patch portion 84. However, the user is permitted to adjust these proportions as needed to achieve a desired dose density or pattern.

In another embodiment, the system automatically adjusts the patch and through beams to optimize dose uniformity through the target mass. The user is permitted to adjust the boundaries of the patch and through portions of the target mass, which causes the system to re-optimize the beam parameters and thereby change the shape and/or thickness of a compensator model being generated for the target mass.

Figure 7:
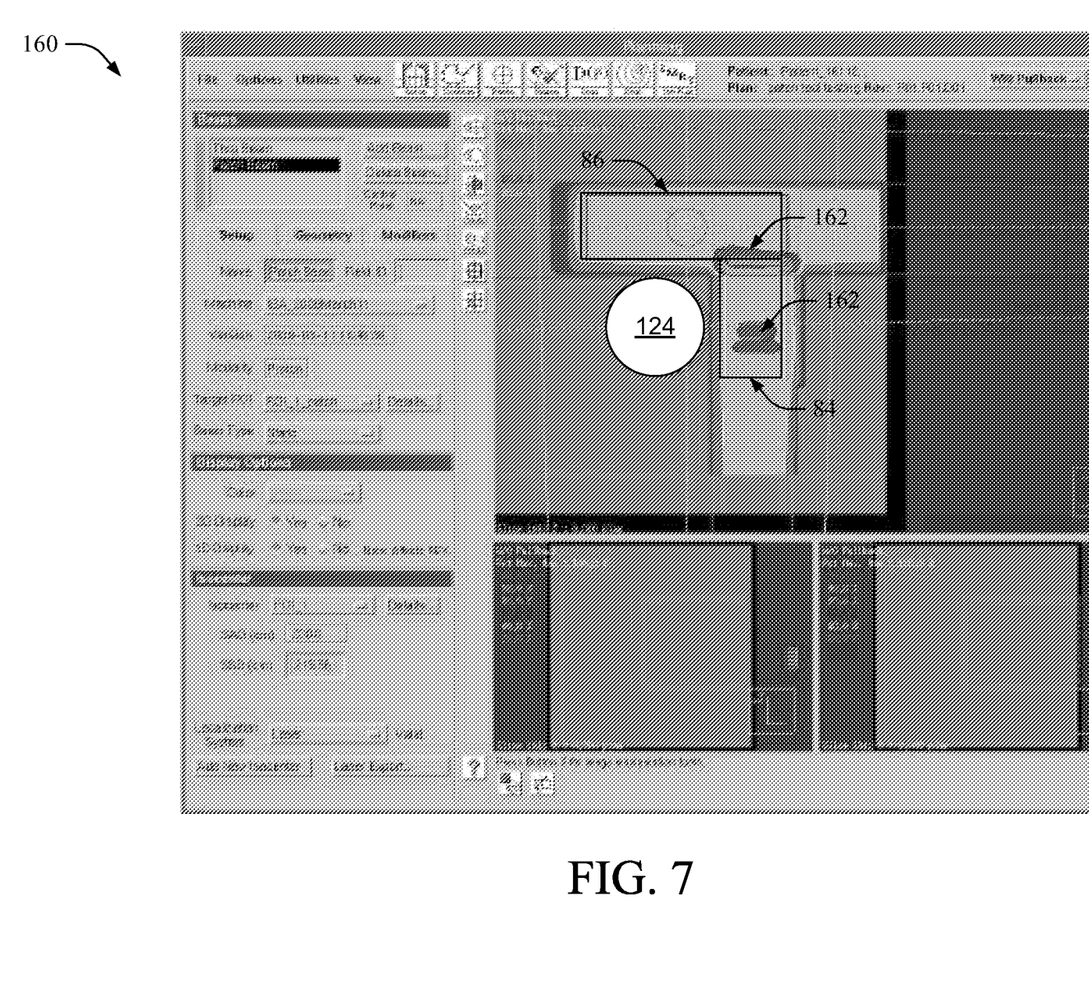
FIG. 7 is a screenshot of a GUI showing a dose distribution of radiation in the patch section and the through section, while preserving the organ, prior to execution of the patch algorithm by the system.

FIG. 7 is a screenshot of a GUI 160 showing a dose distribution 162 of radiation in the patch section 84 and the through section 86, while preserving the organ 124, prior to execution of the patch algorithm (e.g., selection of the patch tool 142 of FIG. 6) by the system.

Figure 8:
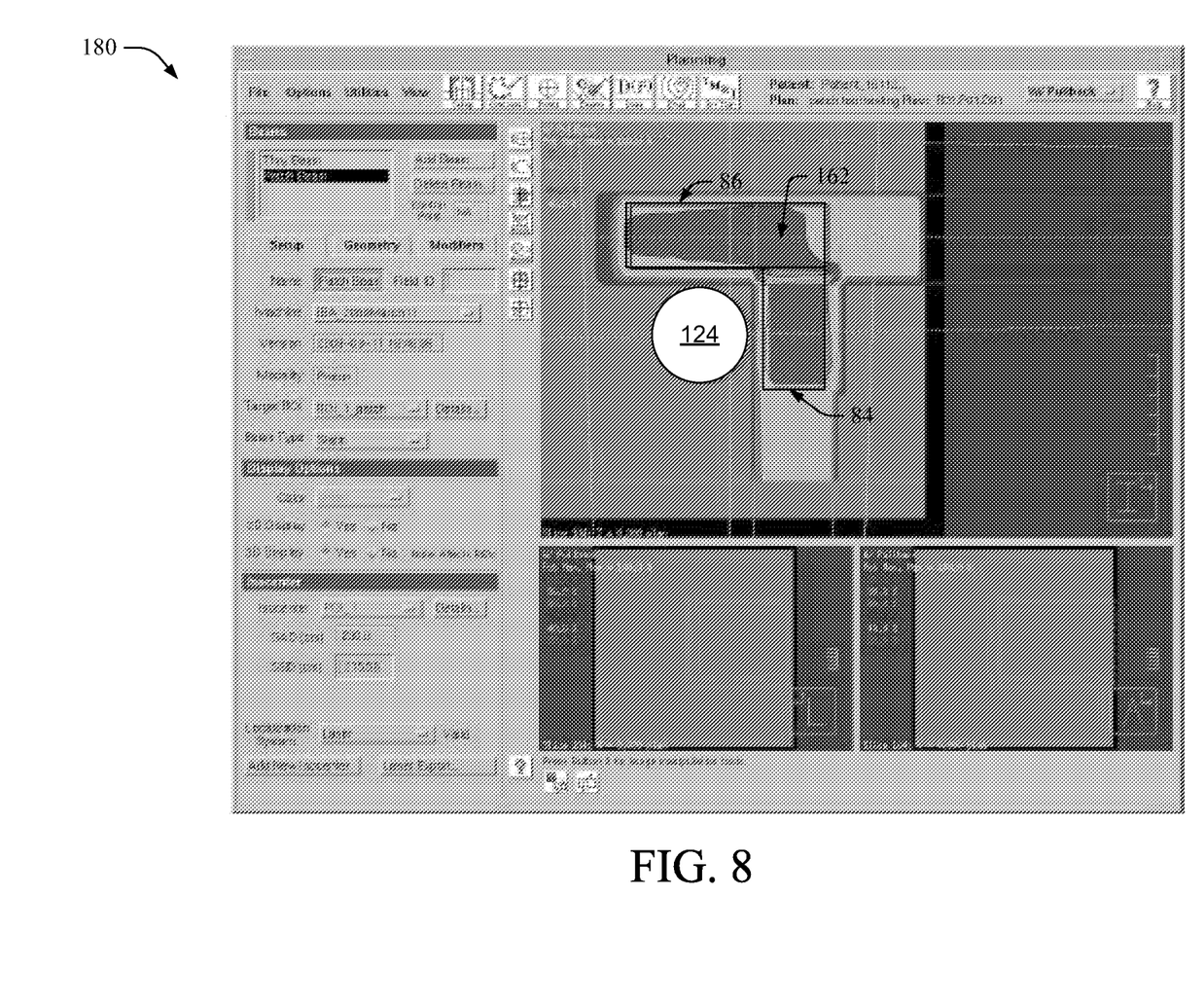
FIG. 8 is a screenshot of a GUI showing optimized dose distribution of radiation in the patch section and the through section, while preserving the organ, after to execution of the patch algorithm by the system.

FIG. 8 is a screenshot of a GUI 180 showing optimized dose distribution 162 of radiation in the patch section 84 and the through section 86, while preserving the organ 124, after to execution of the patch algorithm (e.g., selection of the patch tool 142 of FIG. 6) by the system.

Figure 9:
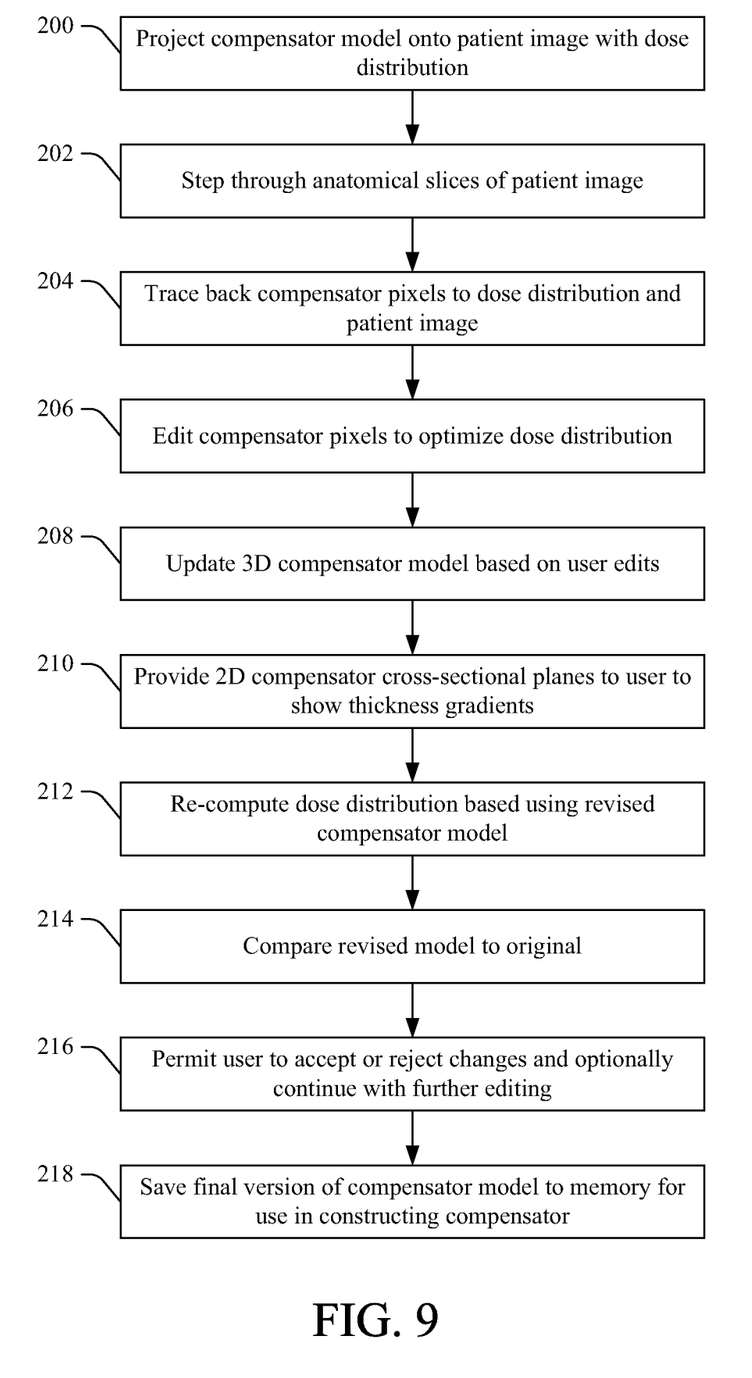
FIG. 9 illustrates a method for computer-aided editing of a 3D compensator model, in accordance with various aspects set forth herein.

FIG. 9 illustrates a method for computer-aided editing of a 3D compensator model, in accordance with various aspects set forth herein. At 200, the compensator is projected onto a patient image along with dose distribution in a beam's eye view 64 display (as seen in FIG. 2). At 202, the user may step through anatomical slices of the patient image, and the projection of the compensator is adjusted accordingly. In this manner, an individual compensator pixel is traced back to the dose distribution and anatomical features, at 204. At 206, the user employs editing tools to edit the compensator pixels in the beam's eye view representation. The user changes the compensator pixels by adding, subtracting, averaging, etc. a value. At 208, the user-entered changes cause an update in a 3-dimensational model of the compensator. 2-dimensional cross-sectional planes of the compensator are presented to the user to aid the user in visualization of the thickness gradients, at 210. After the user edits the compensator, the dose distribution of the beam with the new compensator is re-computed, at 212. At 214, the re-computed dose distribution is compared to the original dose distribution. At 216, the user can "undo" changes, accept changes, and/or or continue with further editing. At 218, when completed, the edits can be saved as a final version of the compensator model, which can be used to construct the compensator.

Figure 10:
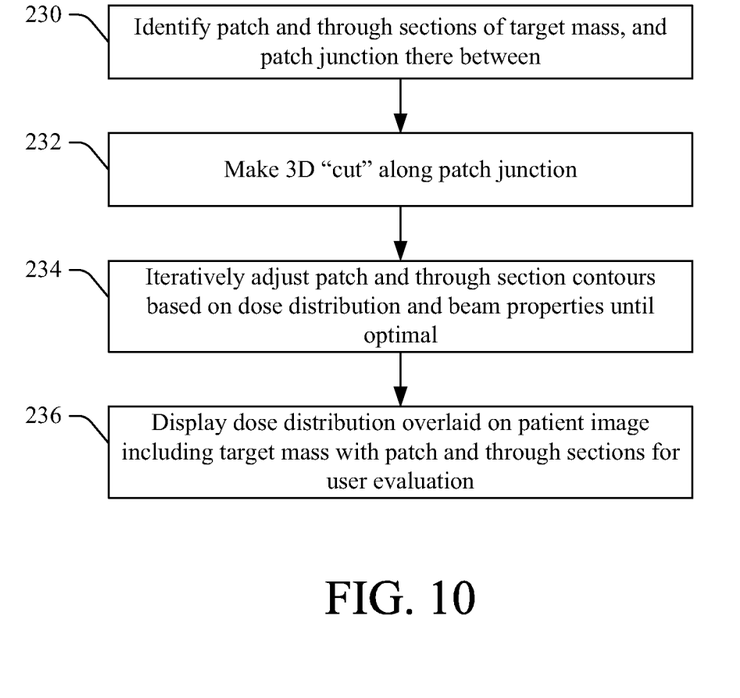
FIG. 10 illustrates a method for optimizing radiation dose for an irregularly-shaped target mass while mitigating unwanted irradiation of a nearby organ or the like, in accordance with various aspects described herein.

FIG. 10 illustrates a method for optimizing radiation dose for an irregularly-shaped target mass while mitigating unwanted irradiation of a nearby organ or the like, in accordance with various aspects described herein. At 230, the target mass is segmented into a "patch" (e.g., distal) region and a "through" (e.g., lateral) region, and a junction therebetween is determined. At 232, a three-dimensional "cut" of the target is made by the algorithm. The contours for the patch and the through beam's targets (e.g., the patch section and the beam section of the target mass, respectively) are treated separately and may be manually or automatically adjusted by the algorithm based on the dose distribution and properties of either the patch or through beams. The user can interact with the regions of interest contours that outline the target as well as the beam parameters to tailor the dose until satisfied, at 234. The user can furthermore display the dose delivered to the target for evaluation and re-optimization, at 236.

Figure 11:
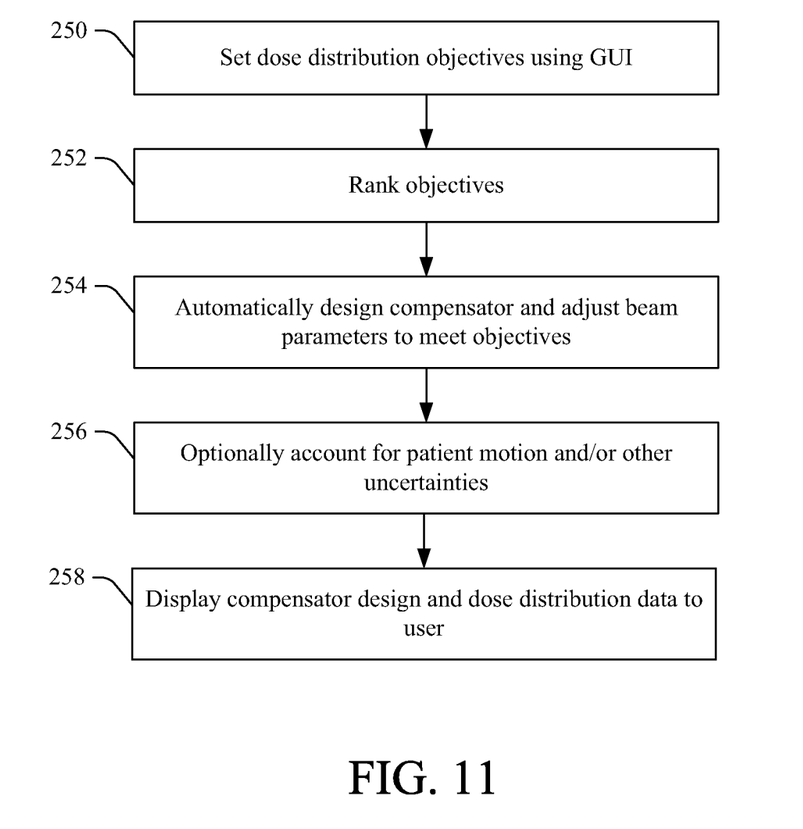
FIG. 11 illustrates a method for performing inverse optimization and design of compensators used in radiotherapy treatments, in accordance with various aspects set forth herein.

FIG. 11 illustrates a method for performing inverse optimization and design of compensators used in radiotherapy treatments, in accordance with various aspects set forth herein. At 250, a user sets goals or objectives for the dose distribution to certain points, organs or regions of the patient (e.g., a target mass and/or surrounding area). The user can specify how much dose as a range, uniformity, or biological equivalent effect a particular region should receive. At 252, the user specifies a rank for each one of the objectives, which conveys the relative importance of meeting that objective. A computer system designs a compensator model and/or adjusts beam parameters including, but not limited to, the range and modulation, margins, and energy of the beam to meet the objectives, at 254. At 256, the user optionally includes uncertainties such as patient motion and image pixel-to-stopping power or density conversion for consideration during compensator design. After the computer system is finished calculating the compensator model, the user is given the opportunity to review the results and adjust the parameters further, which may necessitate a re-optimization, at 258. The method is performed iteratively until the user is satisfied that the compensator model has been optimized, at which point the model is stored and/or output to a compensator machine that constructs the compensator.

The innovation has been described with reference to several embodiments. Modifications and alterations may occur to others upon reading and understanding the preceding detailed description. It is intended that the innovation be construed as including all such modifications and alterations insofar as they come within the scope of the appended claims or the equivalents thereof.

Having thus described the preferred embodiments, the invention is now claimed to be:

1. A ion therapy dose planning system, including:
   a memory that stores:
      an anatomical patient image;
      beam configuration data; and
      at least one initial 3D model of a compensator comprising a plurality of pixels having compensator pixel data wherein the value of each pixel represents the compensator thickness at each pixel;
   a processor in communication with the memory via a bus;
   a graphical user interface including a display and a user input device;
   wherein the processor executes computer-executable instructions stored in the memory, the instructions including:
      computing a radiation dose distribution map for ion beam radiation passing through the at least one model of the compensator using beam configuration data;

displaying on the display, to a user, a projection of the initial 3D model of the compensator on the anatomical image of the patient;

presenting the radiation dose distribution map in a beam's eye view representation;

receiving a user inputted ranking of dose objectives, the dose objectives including:
dose as a range;
dose uniformity; and
dose biological equivalent effect;

receiving user input from the user input device comprising edits to a value of at least one pixel in the beam's eye view representation;

stepping through and displaying a plurality of anatomical slices of the patient image;

in response to receiving the user input edits, editing pixels in the initial 3D model of the compensator for each anatomical slice of the patient image;

generating an optimized 3D model of the compensator by adjusting the initial 3D model of the compensator based on the received user inputted ranking of dose objectives and received edits to a value of at least one pixel; and storing the optimized 3D model of the compensator to the memory or computer-readable storage medium;

wherein the system further includes a compensator constructed from the optimized 3D model of the compensator.

2. The system according to claim 1, the instructions further including:
displaying a plurality of editing tools to a user;
re-computing the radiation dose distribution map based on the optimized 3D model of the compensator; and
displaying the re-computed radiation dose distribution map on the display;
wherein the optimized 3D model of the compensator is projected onto an anatomical patient image with radiation dose distribution map overlaid on the patient image;
wherein the optimized 3D model of the compensator is stored to the memory or computer-readable storage medium upon user approval of the optimized 3D model of the compensator.

3. The system according to claim 1, the instructions further including:
displaying to the user, on the display, a plurality of 2D cross-sectional planes of the 3D model of the compensator showing thickness gradients of the 3D model of the compensator during optimization.

4. The system according to claim 1, the instructions further including:
displaying, on the display, the optimized 3D model of the compensator and the initial 3D model of the compensator to the user for comparison;
permitting the user to accept or reject changes to the initial 3D model of the compensator; and
in response to input from the user on the user input device, iteratively editing the initial 3D model of the compensator.

5. The system according to claim 1, the instructions further including:
outputting an optimized 3D model of the compensator to a machine that constructs the compensator according to the optimized 3D model of the compensator.

6. The system according to claim 1, the instructions further including:
inputting ranked radiation dose distribution objectives with the user input device;
optimizing the initial 3D model of the compensator to meet the dose distribution objectives in the ranked order; and
displaying the optimized 3D model of the compensator and dose distribution map to the user on the display.

7. The system according to claim 1, further including:
a radiation beam generator that generates a radiation beam that is passed through the compensator when treating a patient for whom the compensator is constructed;
wherein the radiation beam generator generates one of an ion beam and a proton beam.

8. The system according to claim 1, the instructions further including:
subsequent to the generating the optimized 3D model, receiving an uncertainty input from the user input device; and
updating the optimized 3D model by accounting for the uncertainty;
wherein the uncertainty includes a patient motion.

9. The system according to claim 8, the instructions further including:
prior to the receiving the uncertainty input from the user input device, adjusting beam parameters including range, modulation, margins, and beam energy.

10. A method of computer-aided 3D model of the compensator optimization for use in radiotherapy treatment, including:
projecting an initial 3D model of the compensator on a patient image of an anatomical region of a patient;
receiving user input edits to the initial 3D model of the compensator comprising edits to at least one pixel;
receiving a user inputted ranking of dose objectives, the dose objectives including:
dose uniformity; and
dose biological equivalent effect;
stepping through and displaying a plurality of anatomical slices of the patient image;
receiving the user input comprising edits to pixels in each anatomical slice of the patient image;
updating the initial 3D model of the compensator based on the user input;
generating an optimized 3D model of the compensator based on the received user inputted ranking of dose objectives and received edits to a value of at least one pixel;
storing the optimized 3D model of the compensator to memory or computer-readable storage medium; and
constructing a compensator from the optimized 3D model of the compensator.

11. The method according to claim 10, further including:
computing a radiation dose distribution map for ion or proton beam radiation passing through the initial 3D model of the compensator into the anatomical region;
displaying, to a user, the initial 3D model of the compensator projected onto anatomical patient image with the radiation dose distribution map overlaid on the patient image;
re-computing the radiation dose distribution map based on the optimized 3D model of the compensator;
displaying the re-computed radiation dose distribution map overlaid on the patient image; and
storing the updated optimized 3D model of the compensator to memory or computer-readable storage medium upon user approval of the optimized 3D model of the compensator.

12. The method according to claim 10, further including:
displaying, to the user, a plurality of 2D cross-sectional planes of the 3D model of the compensator showing thickness gradients of the compensator model.

13. The method according to claim 10, further including:
displaying the optimized 3D model of the compensator and the initial 3D model of the compensator to the user for comparison;
permitting the user to accept or reject changes to the initial 3D model of the compensator; and
iteratively editing the initial 3D model of the compensator until the 3D model of the compensator is optimized.

14. The method according to claim 13, further including:
outputting an optimized 3D model of the compensator to a machine that constructs a compensator according to the optimized 3D model of the compensator.

15. The method according to claim 10, further including:
receiving user input comprising ranked radiation dose distribution objectives;
optimizing the initial 3D model of the compensator to meet the dose distribution objectives in the order in which they are ranked; and
displaying the optimized 3D model of the compensator and dose distribution map to the user.

16. The method according to claim 10, further including:
identifying lateral and distal sections of a computerized model of the target mass and a junction between the lateral and distal sections;
via a user input device, making a virtual cut in the model along the junction;
iteratively adjusting contours of the lateral and distal sections in order to optimize dose distribution; and
displaying the dose distribution map overlaid on a patient image that includes the target mass for user evaluation during dose distribution optimization.

17. The method according to claim 10, further including:
receiving a user input uncertainty; and
updating the optimized 3D model by accounting for the uncertainty;
wherein the uncertainty includes a patient motion.

18. A system that facilitates optimizing a computer-generated 3D compensator model for use in radiotherapy treatment planning, including:
a graphical user interface (GUI) including a display and a user input device;
a processor that executes computer-executable instructions stored in a memory, the instructions including:
displaying on the display, to a user, a projection of an initial compensator model overlaid on an anatomical image of a patient;
presenting on the display a user-selected radiation dose distribution map in a beam's eye view representation;
receiving user input from the user input device comprising edits to the initial compensator model;
receiving user input describing user manipulation of at least one beam configuration parameter;
receiving a user inputted ranking of dose objectives, the dose objectives including:
dose as a range; and
dose biological equivalent effect;
stepping through and displaying a plurality of anatomical slices of the patient image;
receiving the user input comprising edits to pixels in each anatomical slice of the patient image;
generating an optimized compensator model, which achieves the user-selected radiation dose distribution at the target volume, based on the received user input and user inputted ranking of dose objectives; and
storing the optimized compensator model to the memory; and
a compensator constructed from the optimized compensator model.

19. The system according to claim 18, the instructions further including:
receiving a user inputted uncertainty; and
updating the optimized 3D model by accounting for the uncertainty;
wherein the uncertainty includes a patient motion.

20. The system according to claim 18, the instructions further including:
receiving a user inputted uncertainty; and
updating the optimized 3D model by accounting for the uncertainty;
wherein the uncertainty relates to patient motion.

* * * * *